United States Patent
Obara et al.

(10) Patent No.: US 6,756,589 B1
(45) Date of Patent: Jun. 29, 2004

(54) METHOD FOR OBSERVING SPECIMEN AND DEVICE THEREFOR

(75) Inventors: Kenji Obara, Tokyo (JP); Yuji Takagi, Tokyo (JP); Atsushi Shimoda, Tokyo (JP); Ryou Nakagaki, Tokyo (JP); Seiji Isogai, Tokyo (JP); Yasuhiko Ozawa, Tokyo (JP); Hideka Banba, Tokyo (JP); Kenji Watanabe, Tokyo (JP); Chie Shishido, Tokyo (JP)

(73) Assignee: Hitachi, Ltd. (JP)

( * ) Notice: Subject to any disclaimer, the term of this patent is extended or adjusted under 35 U.S.C. 154(b) by 0 days.

(21) Appl. No.: 09/743,560
(22) PCT Filed: Jul. 5, 1999
(86) PCT No.: PCT/JP99/03620
§ 371 (c)(1), (2), (4) Date: Jan. 9, 2001
(87) PCT Pub. No.: WO00/03413
PCT Pub. Date: Jan. 20, 2000

(30) Foreign Application Priority Data

Jul. 10, 1998 (JP) .......................................... 10-195345

(51) Int. Cl.[7] .............................................. H01L 21/66
(52) U.S. Cl. ........................ 250/306; 250/307; 250/311
(58) Field of Search ................................ 250/306, 307, 250/311, 442.11

(56) References Cited

U.S. PATENT DOCUMENTS 5,578,821 A * 11/1996 Meisberger et al. ........ 250/310
5,717,204 A * 2/1998 Meisburger et al. ........ 250/310
6,246,787 B1 * 6/2001 Hennessey et al. ......... 382/141
6,246,788 B1 * 6/2001 Pattikonda et al. ......... 382/147
6,292,582 B1 * 9/2001 Lin et al. .................... 382/149

FOREIGN PATENT DOCUMENTS

JP 11-312716 5/1997
JP 9-139406 11/1999

* cited by examiner

*Primary Examiner*—John R. Lee
*Assistant Examiner*—Anthony Quash
(74) *Attorney, Agent, or Firm*—Townsend and Townsend and Crew LLP

(57) ABSTRACT

During closer inspection with a local defect area being magnified, it is desirable to reduce image acquisition time by making the number of stage moves as few as possible so that a defect can be observed efficiently. To accomplish this, the invention offers a method of observing samples characterized by: acquiring a reference sample image not including any defect on a sample by capturing an image of the sample, based on the information on the defect developed on the sample and detected by an inspection apparatus; adjusting the position of the sample so that the defect will fall within the field of view of image capture, based on the above information; acquiring a defective sample image including the defect on the sample by capturing an image of the sample in the adjusted position; locating the defect on the defective sample image by comparing the reference sample image and the defective sample image; acquiring a magnified image of the defect by capturing a magnified view of the local area where the located defect exists within the field of view of image capture; and displaying the magnified image of the defect on a screen.

10 Claims, 9 Drawing Sheets

Location of defects | Map of Ref. sample image

Location of defects

Map of Ref. sample images

METHOD FOR OBSERVING SPECIMEN AND DEVICE THEREFOR

TECHNICAL FIELD

The present invention relates to sample observation method and equipment intended to be used for an automatic method of closer inspection for a defect developed or a foreign material deposited during the production of semi-conductors.

BACKGROUND ART

As a method of observing samples by which a foreign material or a defect can be viewed in detail, for example, the method described in JP-A-No. 09-139406 has been disclosed.

According to this method, an image pickup device such as a microscope moves to an area where a fault exists, based on the coordinates data obtained beforehand by a discrete fault inspection apparatus, and captures a defective sample image and then captures a magnified view of a foreign material or defect that is located by any means.

Although not clearly mentioned in the above-mentioned JP-A-No. 09-139406 regarding prior art, the above previous method has proved to have some drawbacks as the inventors of the present invention examined this publication. Its drawbacks are as follows:

Judging whether defect extraction processing is successful is possible only by viewing display images that have been acquired, when there is no means for the user to check the validity of the images. If the processing is unsuccessful, we cannot know how it failed. Consequently, the setup for capturing sample images in good conditions of executing the defect extraction takes time.

After a defective sample image including a foreign material or a defect is acquired, when locating the area of the foreign material or the defect or recognizing its shape on the defective sample image with the background pattern behind it, it is desirable to capture a reference sample image not including any fault on the same background pattern together with the defective sample image and compare both images.

When closer inspection is performed by magnifying the local area of the foreign material or defect, if the defective sample image is first captured as is in the above previous method (cited as an example), the stage (platform) on which a sample is placed for inspection must be moved after the first image of the sample is captured so that the area of the reference sample image will fall within the field of view of an image pickup device. After the second image is captured, the exact location of the foreign material or defect is calculated and then the stage must be moved again so that the fault location will fall within the field of view of the image pickup device. Thus, the stage would move frequently to be repositioned and it would take some time to acquire the images.

If the dimensions of the field of view of the microscope when capturing a defective sample image approximate to the stage positioning error, the positioning in an area on the same background as for the defective sample image is difficult and therefore a reference sample image is difficult to acquire.

If capturing a reference sample image corresponding to a defective sample image is always performed, the number of captured images increases in proportion to the number of defects and the time required for acquiring the images increases correspondingly.

An object of the present invention is to provide sample observation method and equipment that enable faster and efficient observation of a defect, solving the problems from the drawbacks involved in prior art.

DISCLOSURE OF THE INVENTION

In order to attain the above object, the present invention offers a method of observing samples in which a view of a desired area of a sample is captured and the thus acquired image is displayed on a first screen, an area to be magnified and observed within the image displayed on the first screen is superimposed on the display image, a magnified view of the displayed area to be magnified and observed within the sample is captured, and the thus acquired magnified image is displayed on a second screen.

In order to attain the above object, the present invention offers a method of observing samples in which the position of a sample is adjusted so that a desired area of the sample will fall within the field of view of observation means for observation, a view of the desired area of the sample is captured at first scale factor and thus a first image is acquired, the first image is displayed on a first screen, an area to be magnified and observed within the first image displayed on the first screen is superimposed on the same screen, a view of the area to be magnified and observed is captured at second scale factor that is larger than the first scale factor and thus a second image is acquired, and the second image is displayed on a second screen.

In order to attain the above object, furthermore, the present invention offers a method of observing samples by using a scanning electron microscope wherein the position of a sample is adjusted so that a desired area of the sample will fall within the field of view of the scanning electron microscope for observation, a view of the desired area of the sample is captured by the scanning electron microscope at first scale factor and a first image is thus acquired, this first image is displayed on a first screen, the first image displayed on the first screen is compared with a reference sample image, an area to be magnified and observed within the first image displayed on the first screen is determined, based on the above comparison, and a magnified image of the area thus determined to be magnified and observed is displayed on a second screen.

In order to attain the above object, furthermore, the present invention offers a method of observing samples characterized by: acquiring a reference sample image not including any defect on a sample by capturing an image of the sample, based on the information on a defect developed on the sample and detected by an inspection apparatus; acquiring a defective sample image including the defect on the sample by capturing an image of the sample, based on the information on the defect developed on the sample and detected by the inspection apparatus; locating the defect on this defective sample image by comparing the reference sample image and the defective sample image; capturing a magnified view of the local area where the located defect exists on the defective sample image, thus acquiring a magnified image of the defect; and displaying this magnified image of the defect on a screen.

In order to attain the above object, furthermore, the present invention offers a method of observing samples characterized by: acquiring a reference sample image not including any defect on a sample by capturing an image of the sample, based on the information on a defect developed go on the sample and detected by an inspection apparatus; adjusting the position of the sample so that the defect will fall within the field of view of image capture, based on the information on the defect developed on the sample and detected by the inspection apparatus; acquiring a defective sample image including the defect on the sample by capturing an image of the sample in the adjusted position; locating the defect on this defective sample image by comparing the reference sample image and the defective sample image; capturing a magnified view of the local area where the located defect exists within the field of view of image capture, thus acquiring a magnified image of the defect; and displaying this magnified image of the defect on a screen.

In order to attain the above object, furthermore the present invention offers a method of observing samples characterized by: acquiring a reference sample image not including any defect on a sample by capturing an image of the sample, based on the information on a defect developed on the sample and detected by an inspection apparatus; acquiring a defective sample image including the defect on the sample by capturing an image of the sample, based on the information on the defect developed on the sample and detected by the inspection apparatus; locating the defect by comparing the reference sample image and the defective sample image; capturing a magnified view of the local area where the located defect exists on the defective sample image, thus acquiring a magnified image of the defect; erasing the background from this magnified image of the defect; and displaying on a screen the magnified image of the defect from where the background has been erased.

In order to attain the above object moreover, the present invention offers an equipment for observing samples, configured to have: image pickup means to capture a view of a sample, thus acquiring an image of the sample; storage means to receive and store data about a desired area of the sample, the view of the area to be captured by the image pickup means, from the external; position control means to control the position of the sample toward the image pickup means, based on the data about the desired area of the sample stored into the storage means; display means to display images of the sample acquired by being captured by the image pickup means; and arithmetic control means to locate a defect on the sample by comparing a plurality of images of the sample zoomed-in by first scale factor and captured by the image pickup means after the sample is positioned by the position control means and make the display means display an image of the defect zoomed-in by second scale factor that is larger than the first scale factor, together with an image including the defect captured at the first scale factor.

In order to attain the above object, moreover, the present invention offers an equipment for observing samples, configured to have: storage means to receive and store the information on a defect developed on a sample acquired through inspection with an external defect inspection apparatus from the defect inspection apparatus; image pickup means to capture a view of the sample, thus acquiring an image of the sample; position control means to control the position of the sample, based on the information on the defect developed on the sample stored into the storage means; defect locating means to locate the defect by comparing an image of the sample not including the defect and an image of the sample including the defect, zoomed-in by first scale factor and captured by the image pickup means after the sample is positioned by the position control means, and display the image including the defect on a screen; and magnified defect display means to display a magnified image of the defect located by the defect locating means, the image captured by the image pickup means at second scale factor that is larger than the first scale factor.

In order to attain the above object, moreover, the present invention offers an equipment for observing samples, configured to have: image pickup means to capture a view of a sample, thus acquiring an image of the sample; position control means to control the position of the sample so that a defect on the sample will fall within the field of view of the image pickup means, based on the information on the defect on the sample acquired through inspection with an external defect inspection apparatus; defect locating means to locate the defect by comparing an image of the sample not including the defect and an image of the sample including the defect, zoomed-in by first scale factor and captured by the image pickup means after the sample is positioned by the position control means, and display on a screen the image of the sample including the thus located defect; and magnified defect display means to display a magnified image of the local area of the sample corresponding to the location of the defect on the image including the defect displayed on the screen of the defect locating means, the image captured by the image pickup means at second scale factor that is larger than the first scale factor.

By displaying a defective sample image on which the result of defect extraction processing is superimposed, the present invention enables the user to verify the validity of the defect extraction.

Processing sequence has been arranged so that the number of stage moves will decrease for more efficient image acquisition. Based on the information on the coordinates of a foreign material or defect, given in advance from a discrete inspection apparatus, a reference sample image corresponding to a defective sample image including the foreign material or defect image is initially acquired. Thereafter, the defective image of the foreign material or defect is captured.

Furthermore, the present invention captures images of samples scaled up by two different scale factors by capturing reference and defective sample images zoomed-in by a lower scale factor, a foreign material or defect is located. A view of the local area where the located foreign material or defect exists is captured, closed up by a higher scale factor. Thereafter, the stage is moved to a position for capturing a reference sample image corresponding to the defective sample image including the foreign material or defect and the reference sample image is captured at the lower scale factor. On the reference sample image of lower scale factor, a template of the area corresponding to the field of view set for image capture by higher scale factor is positioned. By centering the focus on the template area and closing up, a reference sample image of higher scale factor is captured. In this way, the present invention makes it possible that a reference sample image of higher, scale factor corresponding to a defective sample image of higher scale factor be acquired.

Acquired reference sample images are recorded in such a manner that a reference sample image and its area set for image capture, based on the system of coordinates on a chip, assigned for each individual chip, are recorded in a set. When another defect is inspected, if the area for capturing its reference sample image, expressed by coordinates on a chip, is found in the recorded areas of the acquired images, the recorded image is used instead of acquiring the reference sample image. By applying the present invention in this way, the efficiency of image acquisition and inspection would further increase.

BEST MODE FOR CARRYING OUT THE INVENTION

Using the drawings for reference, how the prevent invention is embodied will be explained below.

Figure 1:
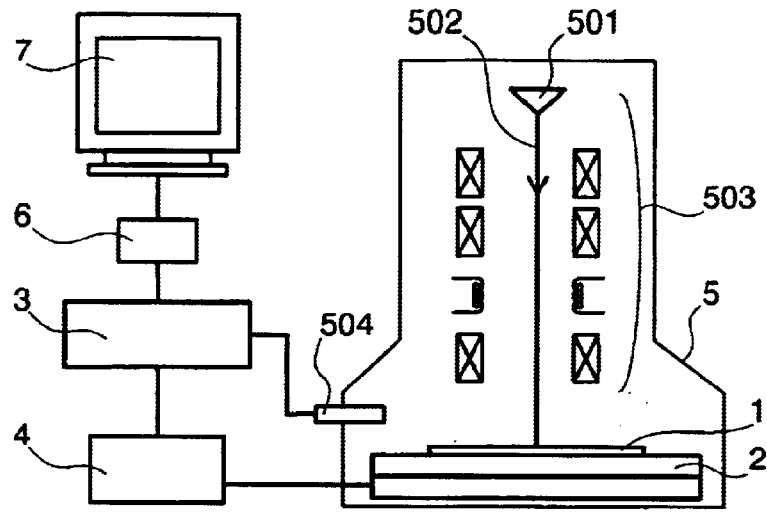
FIG. 1 is a front view of sample observation equipment according to the present invention, showing its structure in outline.

FIG. 1 shows one mode of configuring an image acquisition equipment for carrying out closer defect inspection according to the present invention.

In FIG. 1, reference number 1 is a semiconductor wafer that is subjected to inspection and this wafer is fixed to an X-Y stage 2. The X-Y stage 2 can move in X and Y directions in response to control signals sent from a computer 3 via a controller 4.

Reference number 5 is an image pickup device using a scanning electron microscope (hereinafter referred to as SEM) and this image pickup device captures a magnified view of the semiconductor wafer 1. Specifically, electron beams 502 emitted from an electron source 501 are focused through an electro-optic complex 503 on the semiconductor wafer 1 that is a sample and the wafer 1 is scanned with the beams 502. Secondary electrons reflected from the semiconductor wafer 1 irradiated with the electron beams 502 are detected by a detector 504. In this way, an image of the semiconductor wafer 1 is captured through the SEM.

The image pickup device 5 enables close observation of surface condition anywhere on the semiconductor wafer 1 by controlling the X-Y stage 2. An image captured by the image pickup device 5 is input to the computer 3 and subjected to processing such as defect extraction. The result of processing is displayed on a monitor 7 via a display-switching device 6. The computer 3 may undertake the task of the display-switching device 6.

Figure 2:
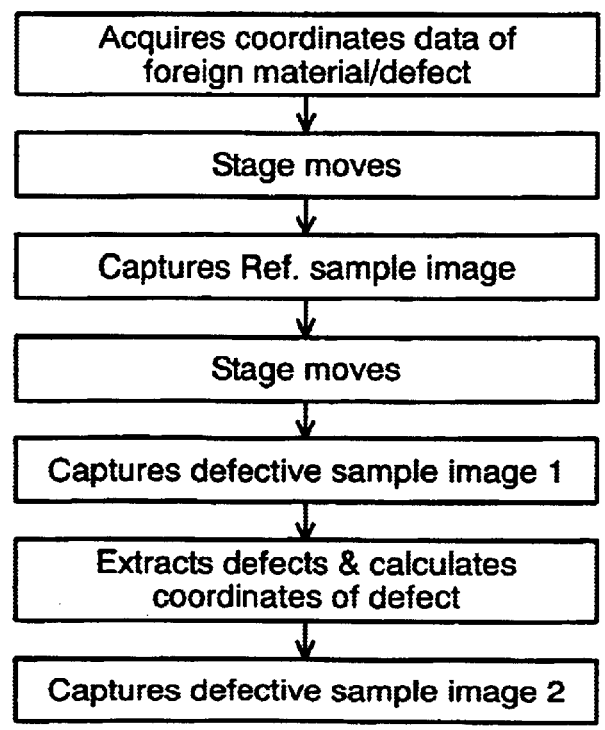
FIG. 2 is a flowchart illustrating a sample observation procedure according to the present invention and FIG. 3 shows the sample images acquired by the sample observation procedure of the present invention.
Figure 3:
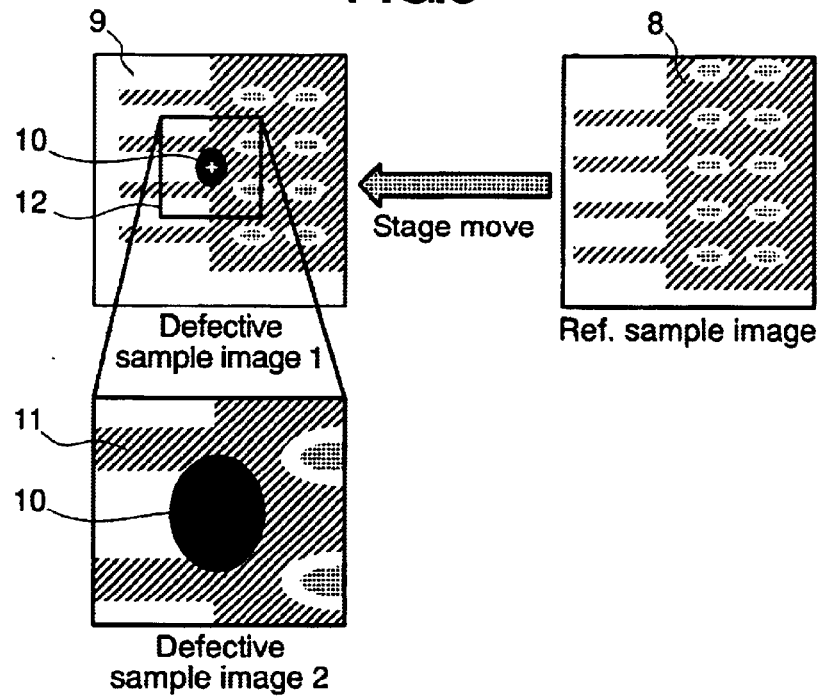

FIG. 2 illustrates an example of the procedure for acquiring images of a sample under inspection and FIG. 3 shows example images acquired by the procedure in FIG. 2.

It is assumed that a semiconductor wafer that is subjected to close inspection has been inspected in advance by a surface defect inspection apparatus which is not shown such as a foreign material inspection apparatus or an appearance inspection apparatus and the coordinates data on the location of a foreign material or a defect has been acquired.

First, the semiconductor wafer 1 to be further inspected is loaded on the X-Y stage 2 and the system of coordinates on the X-Y stage 2 and the system of coordinates on the semiconductor wafer 1 are calibrated by using the semiconductor design data or the acquired defect location data.

Then, the computer 3 sends a command to drive the X-Y stage to the controller 4, based on the defect location coordinates data of the semiconductor wafer 1 stored in advance into the computer 3 at the time of receiving the result of inspection with a surface defect inspection apparatus which is not shown. When receiving this command, the controller 4 drives the X-Y stage 2. In response to the command from the computer 3, the controller 4 first targets a chip adjacent to the chip where a defect exists and positions the stage 2 so that a position corresponding to the position of the defect on the system of coordinates of the adjacent chip will fall within the field of view of the image pickup device 5 at a first scale factor. The image pickup device 5 captures a view of the object zoomed-in at the first scale factor, thereby acquiring an image 8 that is a reference sample image.

At this time, the position on which the image pickup must focus is not limited to the above position on the adjacent chip, but may be set in the corresponding coordinates on the system of coordinates of another chip a few chips apart from the chip where the defect exists. Furthermore, the focus position may be set on a chip having the corresponding pattern of the chip where the defect exists, instead of-being set in the corresponding coordinates on the chip.

The first scale factor is set so that the defect will fall within the field of view of the image pickup when the stage is moved to the defect location with the error of the previously acquired coordinates data of the defect and the stage positioning error being taken into consideration.

Next, the controller 4 repositions the stage 2 so that the defect detected by the surface inspection apparatus will fall within the field of view of the image pickup device 5 set at the first scale factor. The image pickup device 5 captures a view of the chip including the defect, thereby acquiring an image 9 that is a defective sample image.

Then, the acquired image 9 is laid on top of the acquired image 8 with exact alignment by using template matching and a defect location 10 on the defective sample image is calculated by detecting an area of difference between both images.

Next, the scale factor of image pickup is set at a second scale factor that is larger than the first scale factor and the area to be scanned with electron beams is adjusted so that the defect location 10 will be centered in the area. The image pickup device 5 captures a view of this area, thereby acquiring an image 11 that is a defective sample image 2 captured at a higher scale factor with the defect location 10 being in the center of the image. Possible methods of setting the second scale factor of image pickup are as follows: set a desirable scale factor while monitoring the image displayed on the monitor 7 as the area to be scanned with electron beams is narrowed or define the area to be scanned with electron beams in advance by drawing with a cursor or a light pen on the screen of the monitor 7.

By thus acquiring the defective sample image of higher scale factor, any foreign material or defect existing there can be inspected more closely for its shape, surface condition, etc.

In the above process, the defect is located on the sample image captured at the first scale factor after the object position is set so that the defect will fall within the field of view of the image pickup and the scan area of SEM is focused on the located defect position and its surrounding area, assuring that the image of higher scale factor can be acquired. Thus, the image pickup device 5 can surely capture the view of the foreign material or defect within its field of view when capturing the image of higher scale factor.

Because the image 9 is captured after the image 8 is captured in the above procedure, it is not necessary to move the stage 2 after the calculation of the defect location 10 before the image 11 is acquired. Thus, the defective sample image of higher scale factor can be acquired efficiently.

During this process, the area of difference between the image 8 and the image 9 is superimposed on the image 9 displayed on the monitor, so that the user can know how the local area where the defect exists has been determined for extraction.

On the sample image of lower scale factor the area to be observed at higher scale factor within the displayed image is superimposed thereon or simultaneously displayed while this image is displayed. In other words, the filed of view 12 of image pickup at the higher scale factor with the defect location 10 in its center is superimposed on the image 9 displayed or simultaneously displayed with the image 9 displayed on the monitor 7. In this way, the user can be visually informed that what area is extracted and its view is captured as the defective sample image of the higher scale factor.

Furthermore, two or more images of image 8, image 9, image 9 on which the local area of defect or the field of view 12 of image pickup at the higher scale factor is superimposed, and image 9 may be simultaneously displayed on the monitor or monitors 7, so that the user can acquire images while checking the image acquisition operation. A plurality of monitors 7 may be provided on which the images 8, 9, and 11 may be displayed separately or some of them in combination. Alternatively, multiple images may be displayed simultaneously or alternately on one monitor.

The images 8 and 9 may be produced as patterns that are not exactly matching due to the error of positioning the stage 2. In that event, in the process of detecting differential area by laying one image on top of the other image, only the portion of the area that is positively included in both images is effective. The field of view 12 where the image of the object can be captured at the higher scale factor must fall within the field of view for capturing the image 9. That is, the first scale factor and the second scale factor must be correlated to each other. Thus, after the user specifies either the first or second scale factor, the remaining scale factor setting should be restricted within a range.

Figure 4:
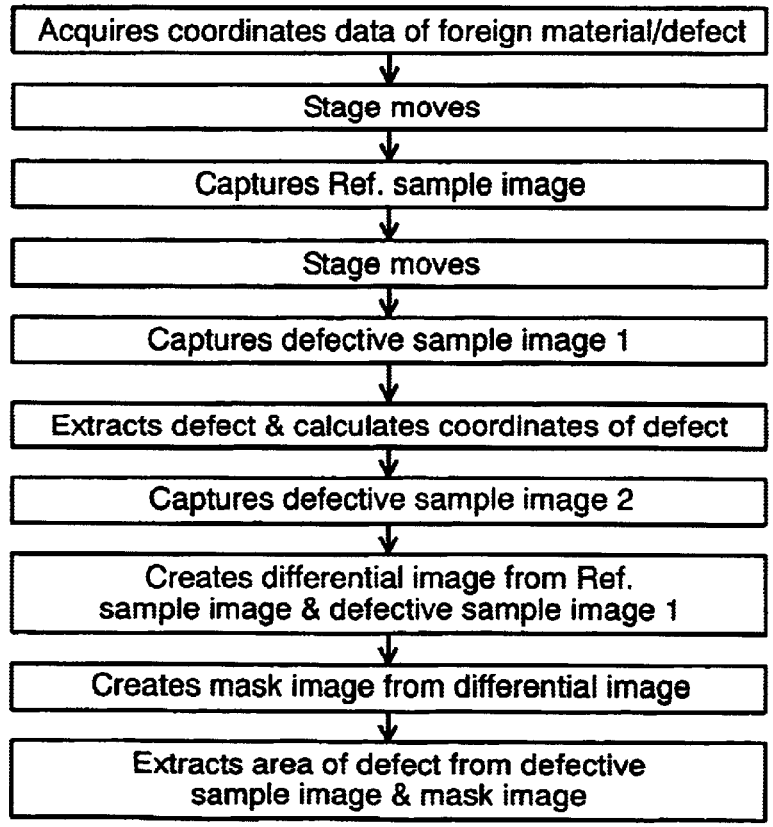
FIG. 4 is a flowchart a flowchart illustrating a sample observation procedure according to the present invention and FIG. 5, FIG. 6, and FIG. 7 show the sample images acquired by the sample observation procedure of the present invention.
Figure 5:
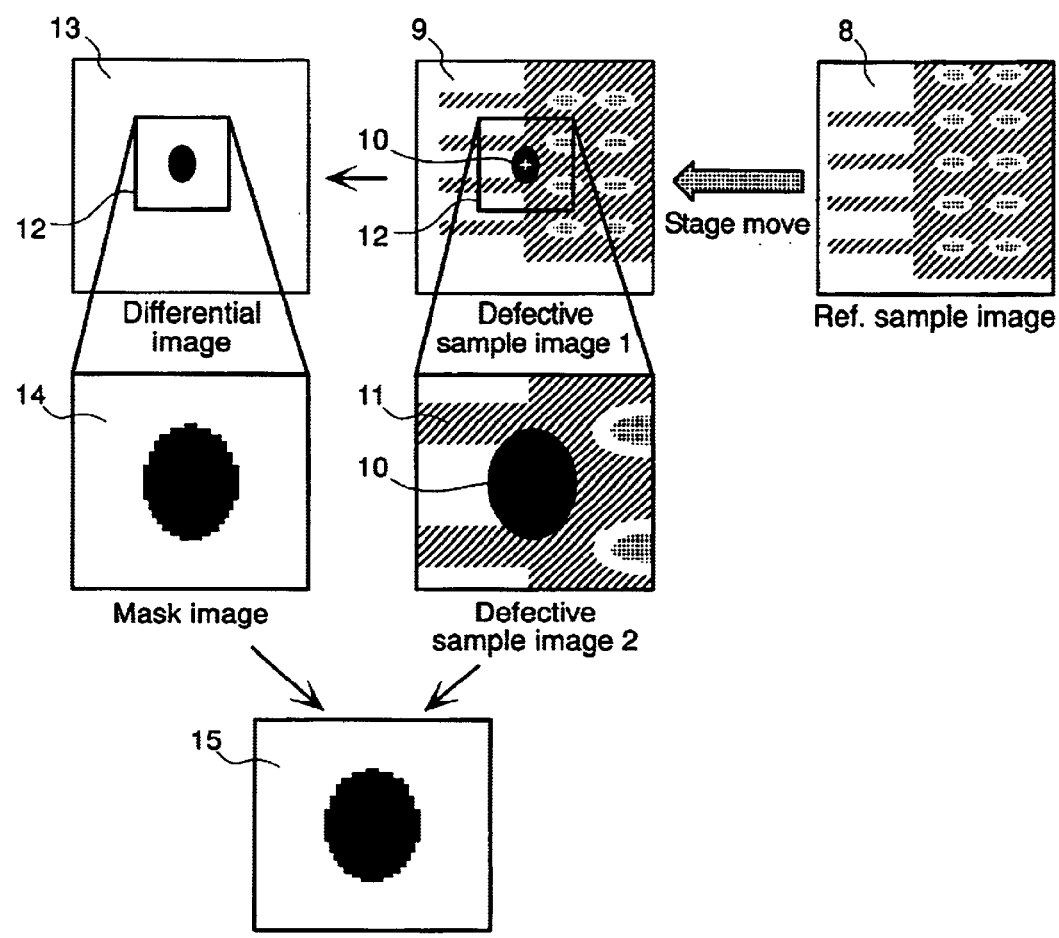

The background of the image 11 can be erased and only the portion of the defect can be extracted such that automatic inspection is carried out in the local area where the foreign material or defect exists. The procedure for this processing is shown in FIG. 4 and example images acquired by this procedure of defect extraction processing are shown in FIG. 5.

In the same way as in the procedure example shown in FIG. 2, the images 8, 9, and 11 are acquired sequentially. In a differential image 13 that represents the area of difference between the image 8 and the image 9, an area 12 that corresponds to the field of view for capturing a defective sample image 2 in a defective sample image 1 is magnified by image processing by the same scale factor as for the defective sample image 2, and a mask image 14 is thus created.

Next, by laying this mask image 14 on top of the image 14, an area corresponding to the difference between the image 11 and the mask image 14 is extracted. By erasing the differential area from the image 11, the background is erased from the image 11 and an image 15 where only the extracted area of the defect remains can be acquired.

By detecting characteristic shape, brightness, texture, etc. of the defect in this extracted area, the analysis of the defect can be performed without intervention of a person.

Figure 6:
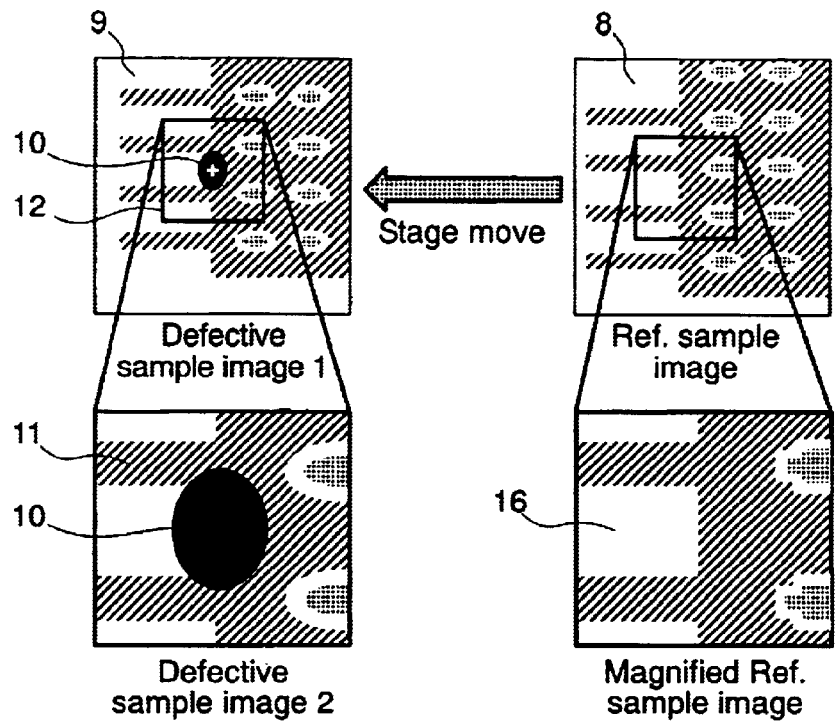

Another method of erasing the background from the image 11 may be used as shown in FIG. 6. In an image 8 that is a reference sample image, an area with the same background as for the focus area 12 for capturing the image 11 in an image 9 that is a defect sample image 1 is magnified by image processing by the same scale factor as for the image 11 and a magnified reference sample image 16 is thus created. Then, the difference between the image 11 and image 16 is extracted.

Figure 7:
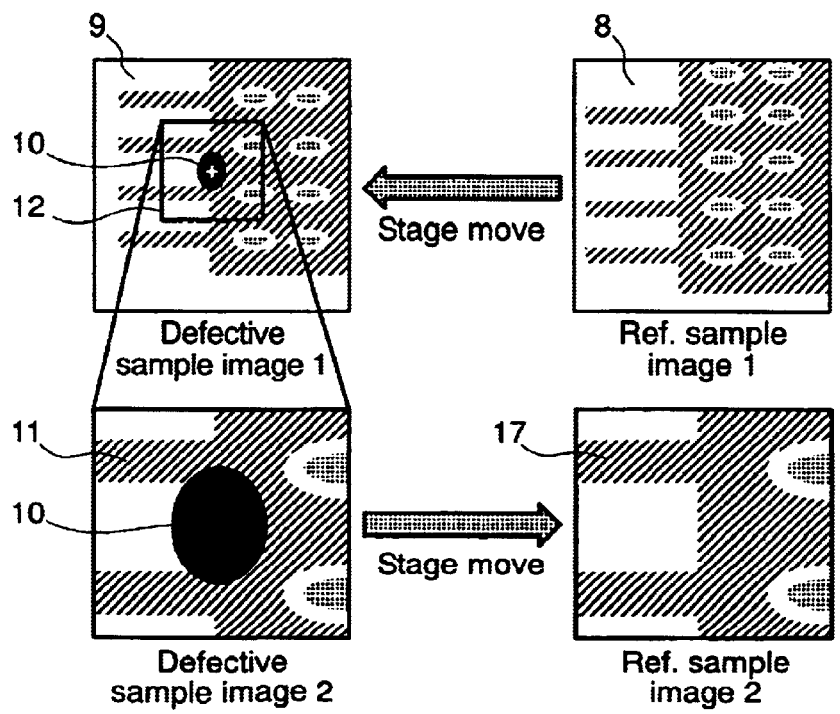

An alternative to the above method may be used as shown in FIG. 7. After the image 11 is captured, a reference target is selected from the chips adjacent to the defect area, within the periphery of a few chips apart from the defect area, or among the areas with the same pattern that the image 11 has. The stage 2 is moved for repositioning so that the target will fall within the field of view of the image pickup device 5. A view of the target is captured by the image pickup device 5 at the same scale factor as for the image 11 and thereby an image 17 that is a reference sample image 2 is acquired. Then, the difference between the image 11 and the image 17 is extracted.

If the size of the field of view for capturing the image 11 approximates to the precision range of moving the stage 2, when the image 17 is captured after the stage 2 is repositioned as in the example shown in FIG. 7, the position of capturing the image may become off the desired position.

Figure 8:
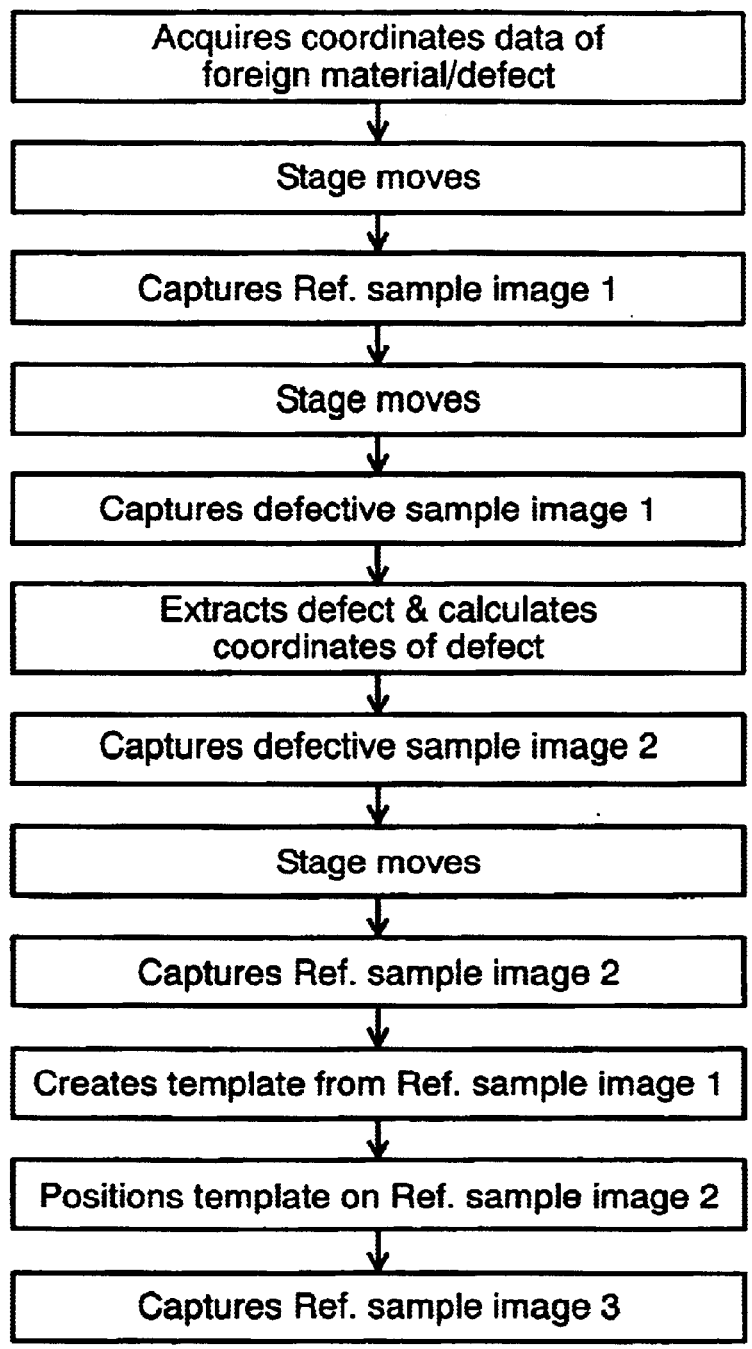
FIG. 8 is a flowchart a flowchart illustrating a sample observation procedure according to the present invention and FIG. 9, FIG. 10, and FIG. 11 show the sample images acquired by the sample observation procedure of the present invention.
Figure 9:
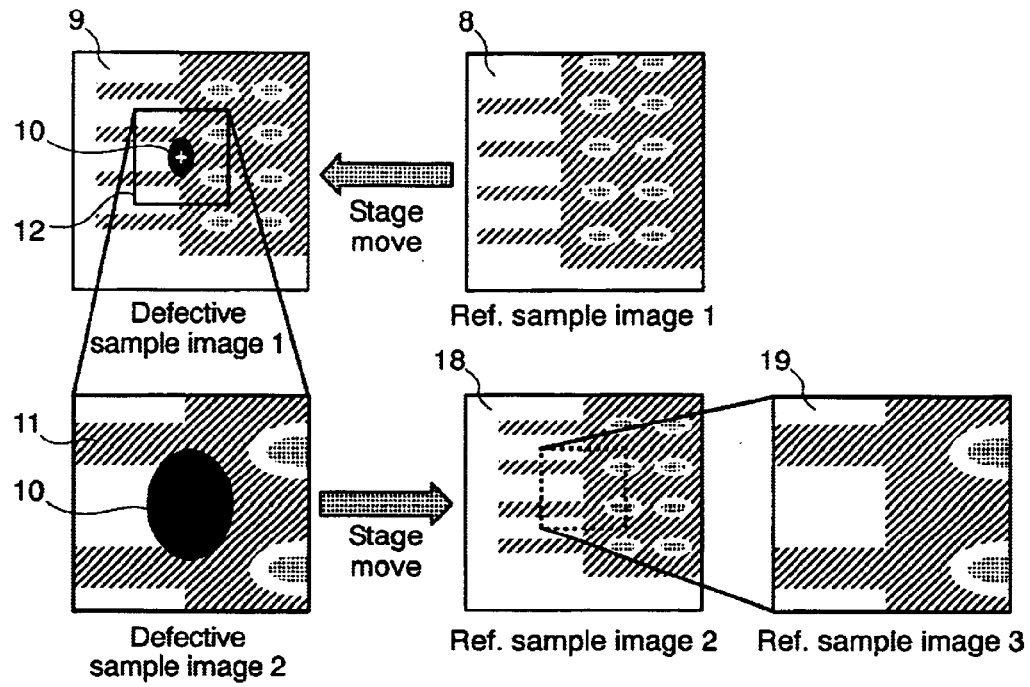

In that event, a reference sample image that exactly matches the image 11 can be acquired in the example procedure shown in FIG. 8. FIG. 9 shows example images acquired by the procedure shown in FIG. 8.

As shown in FIG. 3, correspondingly, the images 8, 9, and 11 are acquired sequentially.

Then, the stage 2 is moved to the position in which the image 8 has been captured and an image 18 that is a reference sample image 2 is captured at the same scale factor as for the image 8.

At this time, the image 8 and the image 18 are not matching in alignment because of the error of positioning the stage 2.

Then, an area on the image 8, corresponding to the focus area 12 in the image 11, is cut out of the image 8 as a template. The template is positioned in the matching position on the image 18.

The template is placed so that its center exactly matches the center of the area where the pattern corresponds to the background of the image 11.

Focusing on the area on which the template is placed, the image pickup device captures an image 19 that is a reference sample image 3 at the same scale factor as for the image 11.

By using the above image capturing sequence, the image 19 corresponding to the image 11 can be captured surely even if the size of the field of view for capturing the image 11 approximates to the precision range of moving the stage 2.

In this image capturing sequence, means for increasing the allowance for the area of the image 18 to include the focus area for capturing the image 19 may be used as follows. An offset of the defect location loin the image 9 from the center of the image 9 is recorded in advance. When the stage 2 is moved to be repositioned for capturing the image 18, the distance over which the stage 2 moves is adjusted by the offset so that the position corresponding to the defect location will be centered in the image 18.

When capturing images, it is advisable to adjust the brightness and contrast controls so that a couple of images zoomed-in by same scale factor, such as the images 8 and 9 the images 18 and 9, and the images 11 and 19 will have the same brightness and contrast.

The above image capturing sequence may be altered as follows. Initially, the image 9 that is a defect sample image 1 is captured, zoomed-in by the first scale factor. After the stage 2 is moved to be repositioned, the image 8 is captured as a reference sample image 1. After calculating the coordinates of the defect location 10 from the images 8 and 9, the image 19 is captured, zoomed-in by a higher second scale factor, and a reference sample image 3 is thus acquired. The stage 2 is moved to the defect location and an image is captured at the first scale factor and the image corresponding to the defective sample image 1 is acquired. After calculating the coordinates of the defect location in the center of the field of view for capturing a defective sample image zoomed-in by the higher scale factor, the image 11 is captured at the second'scale factor as a defective sample image 2.

Figure 10:
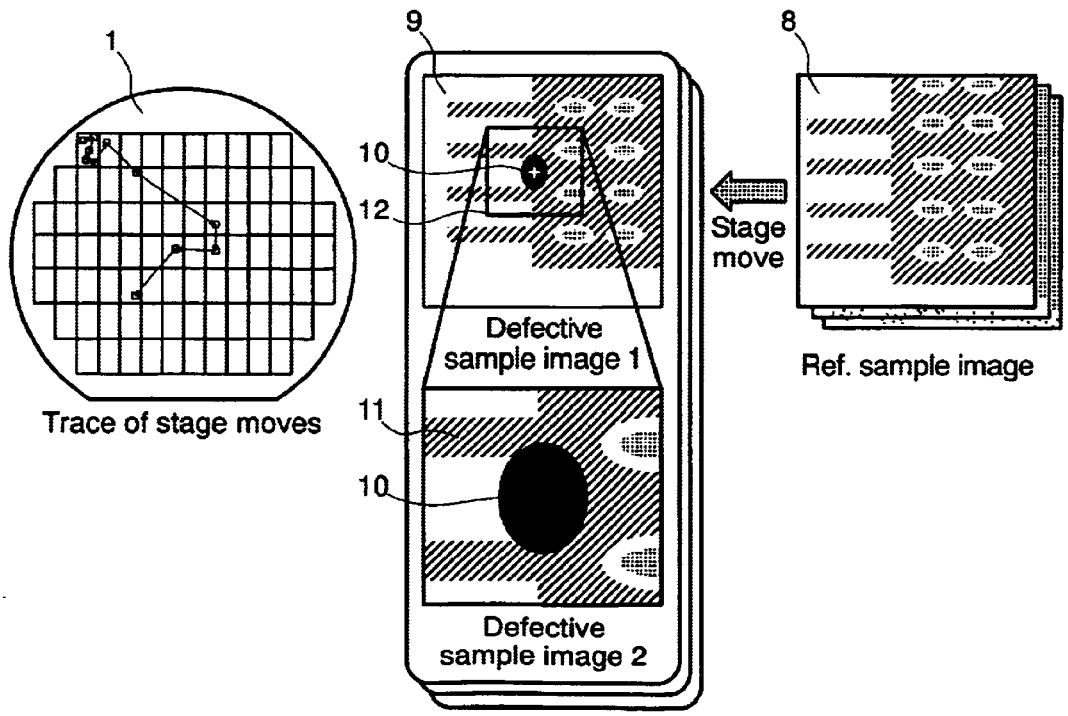

With FIG. 10, the following discusses a case where a plurality of defects are serially inspected by the method of the present invention in the procedure explained with FIGS. 2 and 3, where a reference sample image of higher scale factor is not used.

In this case, by repeating the step of capturing a reference sample image in the processing sequence described in FIGS. 2 and 3, where a reference target is selected from the chips adjacent to the defect area or within the periphery of a few chips apart from the defect area, images 8 for all defects to be inspected are serially captured. Then, the steps of moving the X-Y table 2 for repositioning so that the defect area will fall within the field of view of the image pickup device 5, capturing a view of the defect area zoomed-in by a first scale factor and thus acquiring an image 9, calculating the coordinates of the defect location 10, and capturing a view of the defect zoomed-in by a second scale factor and thus acquiring an image 11 are carried out serially for all the plurality of defects. By capturing the images in this way efficient image acquisition can be performed with the reduced number of stage moves.

Figure 11:
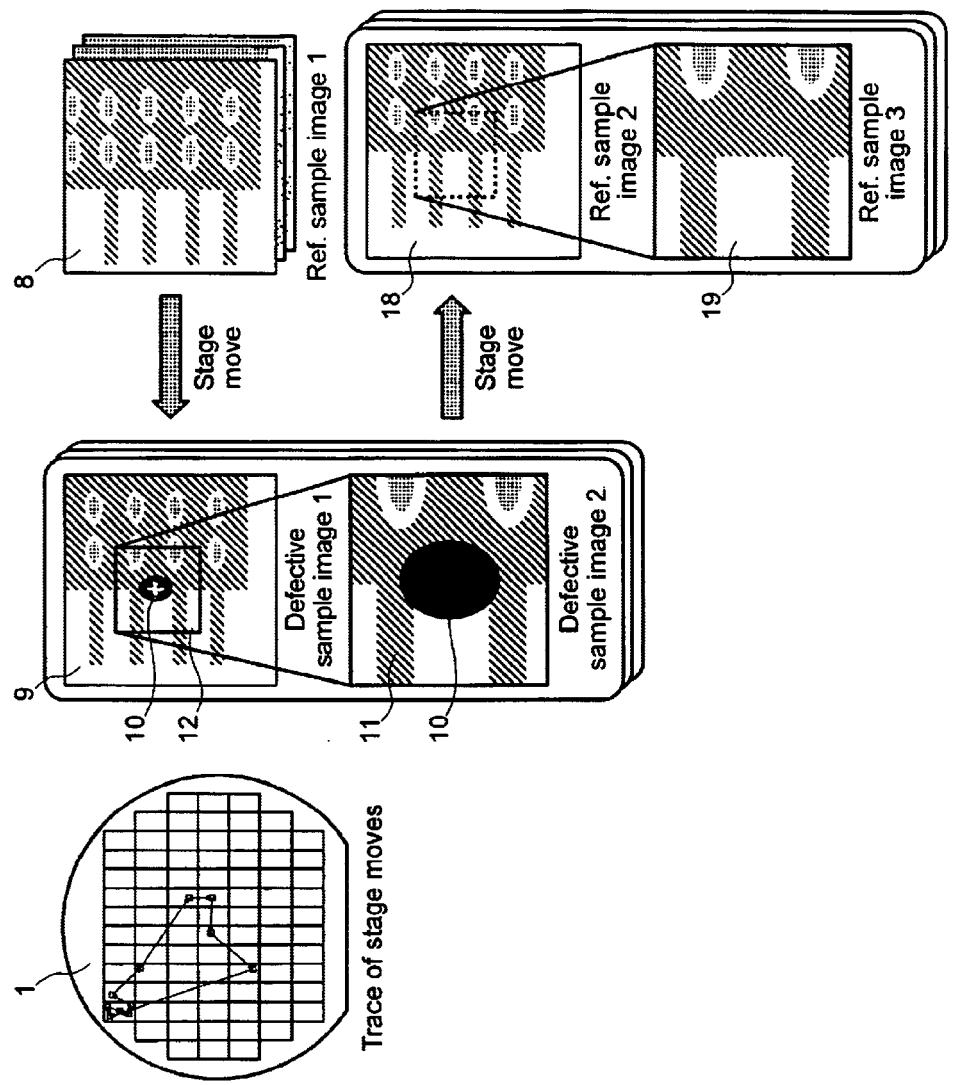

With FIG. 11, the following discusses a case where a plurality of defects are serially inspected by the method of the present invention, which includes the step acquiring reference sample images of higher scale factor.

By selecting a reference target from the chips adjacent to the defect area or within the periphery of a few chips apart from the defect area, first, images 8 for all defects to be inspected are serially captured as reference sample images 1. Then, the operations of moving the X-Y table 2 for repositioning so that the defect area will fall within the field of view of the image pickup device 5, capturing an image 9 of the defect area zoomed-in by a first scale factor, calculating the coordinates of the defect location 10, and capturing an image 11 of the defect are carried out serially and repeated for all the defects.

Next, the following are carried out serially and repeated for all the defects: moving the stage 2 to the position in which the image 8 has been acquired; capturing an image 18 at the same scale factor as for the image 8; cutting a template of the area corresponding to the focus area 12 in the image 9 out of the image 8; positioning the template in the matching position on the image 18; focusing on the area on which the template is placed; and capturing an image 19 at the same scale factor as for the image 11.

When capturing the image 18, however, the stage 2 is not always moved to the position in which the image 8 has been acquired. The stage 2 may be repositioned to any chip that has the same pattern as the background pattern of the image 9.

Figure 12:
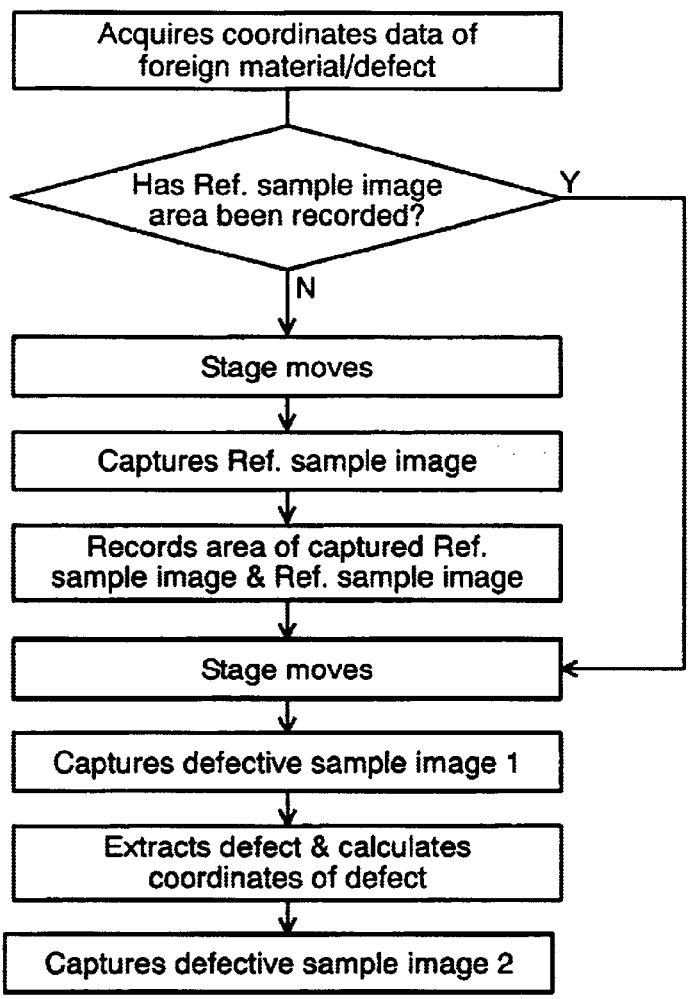
FIG. 12 is a flowchart illustrating a sample observation procedure according to the present invention.
Figure 13:
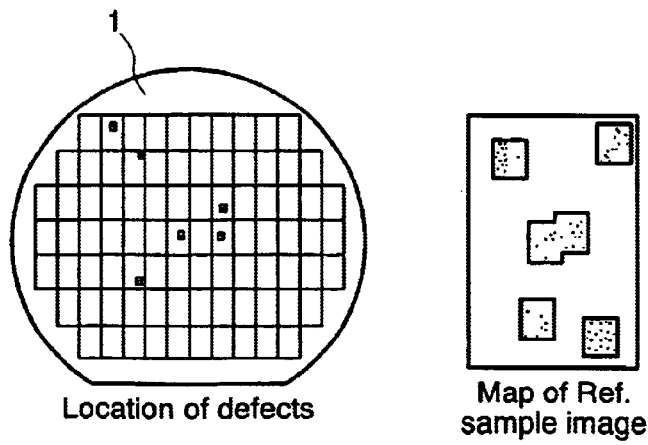
FIG. 13 and FIG. 14 show the locations of defects on a wafer and a map of reference sample images, respectively.

As another example of implementing the present invention, FIGS. 12 and 13 illustrates the procedure for reducing the number of times of acquiring a reference sample image in the processing example shown in FIGS. 2 and 3.

As images 8 are acquired, according to the method described for the processing example shown in FIGS. 2 and 3, a map of the acquired reference sample images is created. In this map, an individual image 8 is recorded, and moreover, the field of view for capturing the image 8, or in other words, the focus area described in terms of the system of coordinates on a chip, defined for each individual chip, is recorded.

When the coordinates of another defect to be inspected more closely are acquired from another inspection apparatus, determination is made as to whether a reference area corresponding to the local area of the defect detected by the coordinates data is found in the areas stored in the map of the reference sample images. If the same area is found in the map, the required area data is retrieved from the image data recorded in the map and used as the image 8 instead of capturing the image 8.

This map of reference sample images may be created to contain the reference sample images zoomed-in by first scale factor or the images zoomed-in by second scale factor, captured at a higher scale factor.

By thus recording acquired reference sample images and reusing them, the number of times of acquiring a reference sample image can be reduced. Particularly, if all reference sample images of required areas are recorded in the map of reference sample images, it is not necessary to execute the reference sample image acquisition step, and consequently the time of image acquisition and closer inspection can be reduced considerably.

Figure 14:
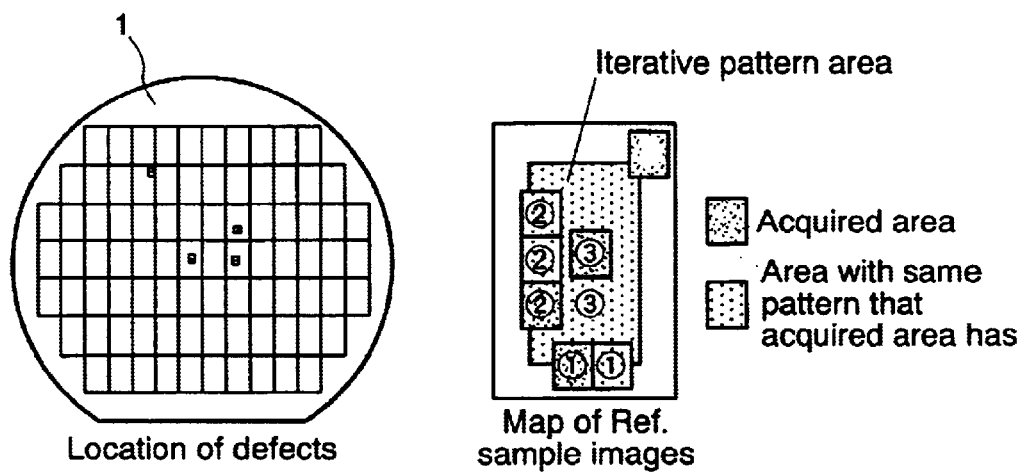

As shown in FIG. 14, in the map of reference sample images, not only an area in which a reference sample image has been captured is recorded, but also an area with the same pattern that an acquired reference sample image has may be recorded as the acquired reference sample image area.

In, for example, an area of iterative pattern, if an image of iterative pattern of one cycle or more is acquired, a reference sample image in any area in the iterative pattern area can be created by combining some portions of the acquired iterative pattern image. Thus, acquiring an image of an iterative pattern area is equivalent to acquiring all reference sample images in the area.

By thus recording a comprehensive area equivalent to acquired reference sample images as acquired area in the map of reference sample images, the number of reference sample images acquired can be decreased and consequently the time required for closer inspection can be reduced.

Alternatively, views of all chip areas may be acquired in advance as reference sample images.

Alternatively, mapping of all sample reference images may be programmed as follows: once a predetermined number of defects have been inspected and a map of reference sample images thereof has been created, views of areas for which reference sample images have not been captured are serially captured as reference sample images.

By programming in this way, when the predetermined number of defects have been inspected, it is assured that all reference sample images are acquired. Therefore, the user can refer to reliable information about the time required for further defect inspection after the completion of inspecting the predetermined number of defects.

Figure 15:
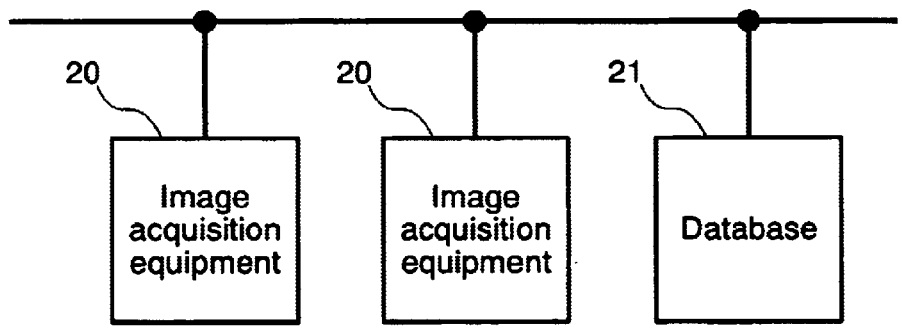
FIG. 15 is a block diagram showing an image data acquisition system configuration in outline according to the invention.

FIG. 15 shows an example configuration for such operation that reference sample image data and the map of reference sample images acquired by the method described above are shared with a plurality of units of image acquisition equipment.

In this configuration, a plurality of units of image acquisition equipment 20 and a server 21 (hereinafter referred to as a database 21) are interconnected via a network. Each image acquisition equipment 20 sends reference sample image data and captured image area data in the map of reference sample images to the database 21. The database 21 has an integrated map of reference sample images into which the reference sample image data sent from the image acquisition equipment 20 is stored.

When each image acquisition equipment 20 executes the inspection of a defect, the equipment searches the map of reference sample images on the database 21 to determine whether a reference sample image corresponding to the defect area has been acquired. If the reference sample image has not been acquired, the image acquisition equipment executes the reference sample image acquisition processing as explained above and sends the acquired reference sample image data to the database 21. If the reference sample image has been acquired, the image acquisition equipment retrieves the appropriate data of the reference sample image from the database 21 and executes closer inspection by using this data.

By using the shared database in this way, reference sample images can be acquired more efficiently. Consequently, the time for closer inspection can be reduced by sharing the reference sample image data.

A single unit of image acquisition equipment may be used to acquire reference sample images.

According to the present invention, as explained above, the user can check to see whether defect extraction processing is successful and know the relation between two scale factors. Therefore, the user can easily perform the setup of image capturing conditions for easy defect extraction and scale factor settings.

The invention can reduce the number of stage moves, which means that defective and reference sample images can be captured efficiently; that is, the image acquisition time can be reduced.

When capturing images of samples closed up by a higher scale factor, which is the process on which the error of positioning the stage has some influence, the present invention enables stable acquisition of defective and reference sample images, so that closer defect inspection can be executed in stable condition.

According to the present invention, a defective sample image is displayed on which the result of defect extraction processing is superimposed, and therefore the user can verify the validity of the defect extraction.

Based on the information on the coordinates of a foreign material or defect, given in advance from a discrete inspection apparatus, a reference sample image corresponding to a defective sample image including the foreign material or defect image is initially acquired. Thereafter, the defective image of the foreign material or defect is captured. Thus, the number of stage moves is fewer and more efficient image acquisition can be achieved.

According to the present invention, furthermore, images of samples are captured, scaled up by two different scale factors, By capturing reference and defective sample images zoomed-in by a lower scale factor, a foreign material or defect is located. A view of the local area where the located foreign material or defect exists is captured, closed up by a higher scale factor. Thereafter, the stage is moved to a position for capturing a reference sample image corresponding to the defective sample image including the foreign material or defect and the reference sample image is captured at the lower scale factor. On the reference sample image of lower scale factor, a template of the area corresponding to the field of view set for image capture by higher scale factor is positioned. By centering the focus on the template area and closing up, a reference sample image of higher scale factor is captured. In this way, the present invention makes it possible that a reference sample image of higher scale factor corresponding to a defective sample image of higher scale factor be acquired.

Reference sample images acquired in the method of present invention are recorded in such a manner that a reference sample image and its area set for image capture, based on the system of coordinates on a chip, assigned for each individual chip, are recorded in a set. When another defect is inspected, if the area for capturing its reference sample image, expressed by coordinates on a chip, is found in the recorded areas of the acquired images the recorded image is used instead of acquiring the reference sample image. Therefore, the present invention further increases the efficiency of image acquisition and inspection.

INDUSTRIAL APPLICABILITY

According to the present invention, as explained above, a foreign material or defect is located by capturing reference and defective sample images zoomed-in by a lower scale factor and a view of the local area where the located foreign material or defect exists is captured, closed up by a higher scale factor. Thereafter, the stage is moved to a position for capturing a reference sample image corresponding to the defective sample image including the foreign material or defect and the reference sample image is captured at the lower scale factor. On the reference sample image of lower scale factor, a template of the area corresponding to the field of view set for image capture by higher scale factor is positioned. By centering the focus on the template area and closing up, a reference sample image of higher scale factor is captured. In this way, a reference sample image of higher scale factor corresponding to a defective sample image of higher scale factor can be acquired. The present invention is suitable for being used method of closer inspection for a defect foreign material deposited during production process.

What is claimed is:

1. Sample observation method comprising steps of:
   acquiring, at a first scale factor, a reference sample image not including any defect on a sample with an imager, based on information on a defect on the sample detected by an inspection apparatus;
   moving the sample in a viewing field of the imager and acquiring a defective sample image including the defect on the sample at the first scale factor with the imager, based on the information on the defect on the sample detected by the inspection apparatus;

locating the defect on the defective sample image by comparing the reference sample image and the defective sample image;

acquiring a magnified image of the located defect at a second scale factor greater than the first scale factor with the imager without moving the sample; and displaying the magnified image of the defect on a screen.

2. Sample observation method according to claim 1, further comprising steps of:

moving the sample to acquire a magnified image of the reference sample with the imager;

acquiring a magnified image of the reference sample at the second scale factor with the imager; and displaying the magnified image of the reference sample on the screen with the magnified image of the located defect.

3. Sample observation method comprising the steps of:

acquiring, at a first scale factor, a reference sample image not including any defect on a sample with an imager, based on information on a defect on the sample detected by an inspection apparatus;

adjusting a position of the sample so that the defect will fall within the field of view of said imager, based on the information;

acquiring a defective sample image including the defect on the sample at the first scale factor by said imager;

locating the defect on the defective sample image by comparing the reference sample image and the defective sample image;

acquiring a magnified image of the located defect at a second scale factor grater than first scale factor with said imager without changing the position of the sample; and displaying the magnified image of the defect on a screen.

4. Sample observation method according to claim 3 further comprising, subsequent to the step of acquiring a magnified image, a step of:

erasing a background from the magnified image of the located defect.

5. Sample observation method according to claim 3, further comprising steps of:

moving the sample to acquire a magnified image of the reference sample with the imager;

acquiring a magnified image of the reference sample at the second scale factor with the imager; and displaying the magnified image of the reference sample on the screan with the magnified image of the located defect.

6. Sample observation method according to any one of claims 3 and 4, wherein the reference sample image and the defective sample images are the images of the sample captured in secondary electrons emanated from the sample by irradiation of a charged particle beam.

7. An apparatus for observing samples, composing:

image pickup means for acquiring an image of a sample;

storage means to store information of an area to be observed on the sample;

a position controller to control a position of the sample with respect to the image pickup means, based on the information stored in the storage means;

display means to display images of the sample acquired by the image pickup means; and control means to locate a defect on the sample by comparing a plurality of images of the sample captured by the image pickup means at a first scale factor after the sample is positioned by the position controller and to control the image pickup means to acquire located defect image at a second scale factor greater than the first scale factor without changing the position of the sample, wherein the plurality of image includes a reference sample image acquired by positioning the sample so that a reference area that is absent any defect is within viewing field of the image pickup means, wherein the plurality of the images a defect sample image acquired by positioning the sample to a defect position such that a defect area that included at least one defect is positioned within the view field of the image means, wherein the located defect image is acquired by imaging an area of the sample determined based on a comparison of the reference sample image with the defect sample image without repositioning the sample from the defect position.

8. An apparatus for observing samples, comprising:

storage means to store information on a defect on a sample defected by an external defect inspection apparatus;

image pickup means for acquiring image of the sample;

position control means to control a position of the sample, based on the information stored in the storage means;

defect locating means to locate the defect by comparing an image of the sample not including the defect and an image of the sample including the defect, wherein both of the images are acquired at a first scale factor by the image pickup means after the sample is positioned by the position control means; and display mean to display an image of the defected locating means and capture by the image pickup means at a second scale factor that is greater than the first scale factor without changing the position of the sample.

9. An apparatus for observing samples, comprising:

image pickup means for acquiring an image of the sample;

position control means to control a position of the sample so that a defect on the sample will fall within the field of view of the image pickup means, based on information on the defect on the sample detected by an external defect inspection apparatus;

defect locating means to locate the defect by comparing an image of the sample not including the defect and an image of the sample including the defect, wherein both of the images are acquired by the image pickup means at a first scale factor after the sample is positioned by the position control means; and display means to display an image of the defect located by the defect locating means and captured by the image pickup means at a second scale factor that is greater than the first scale factor without changing the position of the sample.

10. Sample observation equipment according to any one of claims 7, 8, and 9, wherein the image pickup means is a scanning electron microscope.

* * * * *